United States Patent
Arunachalam et al.

(10) Patent No.: US 9,708,387 B2
(45) Date of Patent: Jul. 18, 2017

(54) METHODS FOR PRODUCING RECOMBINANT FACTOR VIII CHAINS FROM NON-FILAMENTOUS FUNGI, THEIR FUNCTIONAL RECONSTITUTION AND APPLICATIONS THEREOF

(71) Applicants: CENTRE FOR BIOSEPARATION TECHNOLOGY-VIT, Vellore, Tamil Nadu (IN); Christian Medical College, Vellore, Tamil Nadu (IN)

(72) Inventors: Vijayalakshmi Mookambeswaran Arunachalam, Tamil Nadu (IN); Vignesh Narasimhan Janakiraman, Tamil Nadu (IN); Krishnan Venkataraman, Tamil Nadu (IN); Sudheer Reddy Aswatha Reddy, Tamil Nadu (IN); Satheeshkumar Padikkara Kutty, Tamil Nadu (IN); Sukesh Chandran Nair, Tamil Nadu (IN); Alok Srivastava, Tamil Nadu (IN)

(73) Assignee: CENTRE FOR BIOSEPARATION TECHNOLOGY-VIT, Vellore (IN)

( * ) Notice: Subject to any disclaimer, the term of this patent is extended or adjusted under 35 U.S.C. 154(b) by 0 days.

(21) Appl. No.: 14/427,622

(22) PCT Filed: Sep. 11, 2013

(86) PCT No.: PCT/IB2013/058449
§ 371 (c)(1),
(2) Date: Mar. 11, 2015

(87) PCT Pub. No.: WO2014/041483
PCT Pub. Date: Mar. 20, 2014

(65) Prior Publication Data
US 2015/0225472 A1  Aug. 13, 2015

(30) Foreign Application Priority Data
Sep. 11, 2012  (IN) .......................... 3777/CHE/2012

(51) Int. Cl.
A61K 38/37    (2006.01)
C07K 14/755   (2006.01)
C12P 21/02    (2006.01)
C12N 15/81    (2006.01)
C07K 1/22     (2006.01)

(52) U.S. Cl.
CPC .............. C07K 14/755 (2013.01); C07K 1/22 (2013.01); C12N 15/815 (2013.01); C12P 21/02 (2013.01)

(58) Field of Classification Search
None
See application file for complete search history.

(56) References Cited

U.S. PATENT DOCUMENTS 5,693,499 A * 12/1997 Yonemura ............ C07K 14/755
                                                            435/320.1
2006/0099685 A1  5/2006 Yallop et al.
2012/0052530 A1  3/2012 Gerngross et al.

FOREIGN PATENT DOCUMENTS

CN     1361178 A       7/2002
WO     WO 2011046855 A1 *  4/2011  ......... C07K 14/4715

OTHER PUBLICATIONS

Takeshima et al., Thromb. Haemost. 89:788-794, 2003.*
Ngo et al., Structure 16:597-606, 2008.*
GenBank EU285586.1, Extracellular expression vector pKanB alpha, complete sequence, Apr. 23, 2008, [Retrieved from the Internet Apr. 2, 2014: <http://www.ncbi.nlm.nih.gov/nucleotide/164708570?report=genbank&log$=nuclalign&blast_rank=1&RID=KS4VR4UR01R>]; nucleotides 1212-1234, 2 pages.
Invitrogen, pPICZa A, B, and C Pichia expression vectors for selection on Zeocin and purification of secreted, recombinant proteins, Cat. No. V195-20, Manual part No. 25/0150, Jul. 7, 2010, 48 pages.
International Searching Authority, International Search Report for International Application No. PCT/IB13/58449, Apr. 16, 2014, 5 pages.

* cited by examiner

Primary Examiner — David J Steadman
(74) Attorney, Agent, or Firm — McCoy Russell LLP

(57) ABSTRACT

A process of producing heavy chain peptide and/or light chain peptide of recombinant Factor VIII protein includes using the *Pichia pastoris* expression system. A process of producing a functional recombinant Factor VIII protein by reconstituting the Heavy chain and Light chain produced using said *Pichia pastoris* expression system. The said functional recombinant Factor VIII protein shows improved activity and therefore is used in the management of haemophilia.

12 Claims, 6 Drawing Sheets

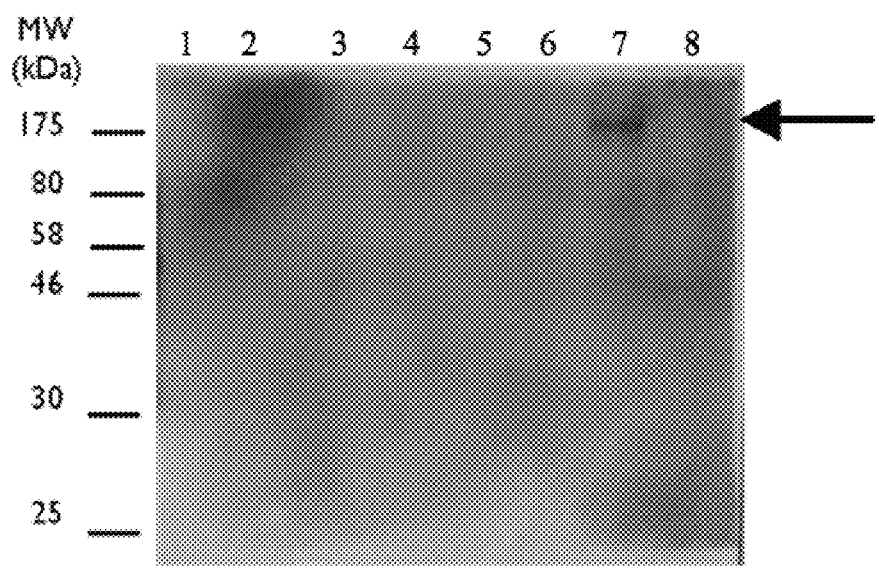
FIG. 2
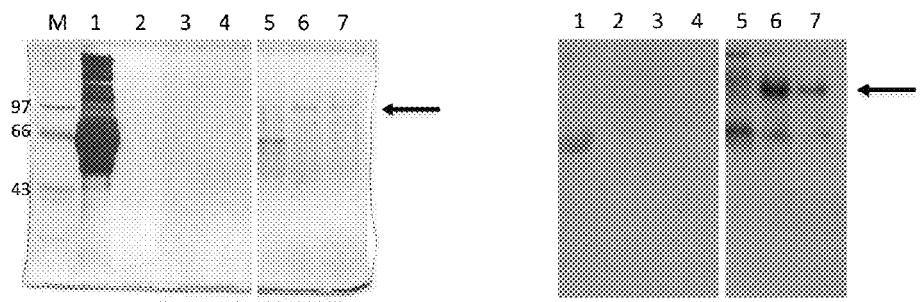
FIG. 3A
FIG. 3B

US 9,708,387 B2

METHODS FOR PRODUCING RECOMBINANT FACTOR VIII CHAINS FROM NON-FILAMENTOUS FUNGI, THEIR FUNCTIONAL RECONSTITUTION AND APPLICATIONS THEREOF

INCORPORATION BY REFERENCE OF ELECTRONICALLY SUBMITTED MATERIAL

Incorporated by reference in its entirety is a computer-readable nucleotide sequence listing submitted herewith and identified as follows: 19,483 bytes ASCII (Text) file named "Substitute_Sequence_Listing_KNS16303PCTUS," created Oct. 6, 2016.

FIELD OF THE INVENTION

The present disclosure is in the field of haemophilia therapeutics, particularly recombinant Factor VIII protein products. The present disclosure relates specifically to a process of producing heavy chain peptide and/or light chain peptide of recombinant Factor VIII protein using non-filamentous fungi, particularly *Pichia pastoris*. The disclosure further relates to a process of producing a functional recombinant Factor VIII protein by reconstituting the Heavy chain and Light chain produced using said *Pichia pastoris* expression system. The functional recombinant Factor VIII protein of the present concept shows improved activity and therefore is used in the management of haemophilia.

BACKGROUND OF THE INVENTION

Factor VIII: C (FVIII: C) is an essential blood coagulation factor, whose absence or loss of activity results in the clotting disorder Haemophilia A. Activated factor VIII: C acts as a cofactor to activated factor IX, which together activate factor X in the coagulation cascade.

Factor VIII: C (FVIII: C) is a plasma protein essential for blood coagulation whose deficiency or defective formation results in the blood clotting disorder known as Haemophilia A (Lenting et. al., 1998). FVIII: C is synthesized as a 300-kd precursor protein comprising of six domains: A1, A2, B, A3, C1 and C2. In the plasma, upon limited proteolysis by thrombin, it circulates as a heterodimer consisting of the heavy chain (A1-A2-B domains) and light chain (A3-C1-C2 domains) linked by a Calcium (II) ion through the A1 and A3 domains. This FVIII: C heterodimer circulates in the plasma as a non-covalent complex with von Willerbrand Factor (vWF), a large ~220 kDa multimeric protein (Sadler, 1998). The association of FVIII: C with vWF results in its increased circulatory half-life, by avoiding premature proteolytic activation of factor VIII: C (Saenko et. al., 1999). While still in circulation, the heavy chain is further proteolysed where the B-domain is deleted. FVIII: C is activated by further proteolysis of the heavy chain resulting in a heterotrimer consisting of A1, A2 and A3-C1-C2 subunits (Shen et. al., 2008). Active FVIII: C (FVIII: Ca) associates with activated Factor IX (FIXa) to form the "X-ase" (ten-ase) complex which activates Factor X (FXa). FXa, along with activated Factor V (FVa), activates the prothrombinase complex that converts prothrombin to thrombin, resulting in a blood clot (Wang et. al., 2003). However, FVIII: Ca quickly loses its activity through one of the following mechanisms: (i) by spontaneous dissociation of the A2 subunit from the A1-A3C1C2 complex (Fay and Smudzin, 1992), or (ii) by proteolytic degradation by activated protein C, thrombin, FXa, FIXa, etc. (Fay, 2004). FVIII: Ca is thus quickly cleared from the system.

The light chain of factor VIII: C has sites for phospholipid binding and vWF binding in the C2 domain (Nogami et. al., 2007), while the heavy chain is primarily responsible for the correct orientation of the factor VIII: C light chain-heavy chain complex and also for binding to factor IXa through the A1 domain at residues in the region between amino acids 558-565 and residues near amino acid 712 (Ngo et. al., 2008), which is essential to provide coagulation activity.

Haemophilia A is caused by either absence or the loss of factor VIII: C activity, which could be due to a number of reasons, including genetic defects resulting in the improper folding/secretion of factor VIII: C (White and Shoemaker, 1989) or development of auto-antibodies against factor VIII: C (Shima, 2006). To counter the deficiency or the loss of factor VIII: C activity observed in haemophilia patients, FVIII: C is administered as plasma concentrates (Marchesi et. al., 1972), or as recombinant factor VIII: C expressed using mammalian cells (Wood et. al., 1984; Kaufman et. al., 1988). The purification of factor VIII: C from plasma-derived sources is limited by two major bottlenecks: the scarcity in obtaining sufficient amounts of plasma from healthy donors to purify factor VIII: C; and the risk of viral contamination, though methods to reduce the risk of viral contamination have evolved through solvent/detergent extraction methods (Mannucci, 2010). These considerations made recombinant factor VIII: C an alternate option for the treatment of Haemophilia A.

Recombinant factor VIII: C preparations were first made in 1980s (Wood et. al., 1984). Furthermore, it has been shown that the B-domain of FVIII: C is dispensable for its coagulation activity (Eaton et. al., 1986). A number of B-domain deleted factor VIII: C products like ReFacto®/Xyntha™ (Wyeth Pharma) are currently available in the market. However, this B-domain deleted factor VIII: C (BDD-FVIII: C) is still a large molecule of five domains thus making its expression difficult.

Conventional Haemophilia A therapy involves the infusion of either plasma-derived Factor VIII: C or recombinant Factor VIII: C expressed in mammalian expression systems. The scarcity and risk in obtaining plasma-derived Factor VIII: C, the difficulty in expressing full length recombinant Factor VIII: C demands newer methods and or alternate strategies for producing functional Factor VIIIC therapeutic molecule.

The present disclosure aims at overcoming the drawbacks of the prior art by making use of the *Pichia pastoris* expression system to generate functional factor VIII chains.

SUMMARY OF THE PRESENT INVENTION

Accordingly, the present disclosure relates to a DNA construct comprising polynucleotide sequence having at least 95% sequence identity to sequence as set forth in SEQ ID NO. 1; A DNA construct comprising polynucleotide sequence having at least 95% sequence identity to sequence as set forth in SEQ ID NO. 3; A vector comprising polynucleotide sequence as set forth in SEQ ID NO. 1, SEQ ID NO. 3 or a combination thereof; A host cell comprising polynucleotide sequence of SEQ ID NO. 1, SEQ ID NO. 3 or a combination thereof; A host cell comprising the vector comprising polynucleotide sequence as set forth in SEQ ID NO. 1, SEQ ID NO. 3 or a combination thereof; A process for obtaining heavy chain peptide or light chain peptide of recombinant Factor VIII protein or a combination thereof, said method comprising act of culturing cells of non-filamentous fungi comprising nucleotide sequence corresponding to the peptide to obtain said peptide; A process for obtaining recombinant factor VIII protein, said process comprising acts of: (a) introducing the polynucleotide sequence of claim 1 or the polynucleotide sequence of claim 3 or a combination thereof into a host cell to obtain corresponding polypeptides individually or in combination; or (b) introducing the vector as claimed in claim 5 into a host cell to obtain corresponding polypeptides individually or in combination; and (c) reconstituting the polypeptides produced by step (a) or (b) to obtain the recombinant Factor VIII protein; and a recombinant factor VIII protein obtained by said process.

BRIEF DESCRIPTION OF THE DRAWINGS

In order that the invention may be readily understood and put into practical effect, reference will now be made to exemplary embodiments as illustrated with reference to the accompanying figures. The figures, together with a detailed description below, are incorporated in and form part of the specification, and serve to further illustrate the various embodiments, principles and advantages, in accordance with the present disclosure where:

FIG. 2 is a photograph of a gel depicting a western blot analysis of expression of heavy chain of factor VIII: C in *Pichia pastoris* GS115, wherein lanes 1-3 correspond to the following uninduced cultures; cell control, vector control, and heavy chain clone HC1, respectively, and further wherein lanes 5-7 correspond to the following cultures induced for 90 hrs; cell control, vector control and heavy chain clone HC1, respectively;

FIG. 3A is a photograph of a gel depicting an SDS-PAGE analysis of expression of light chain of factor VIII: C in *Pichia pastoris* GS115, wherein lanes 2-4 correspond to the following uninduced cultures; heavy chain clone HC1, and two light chain clones LC1 & LC2, respectively, and further wherein lanes 5-7 correspond to the following cultures induced for 90 hrs; heavy chain clone HC1, and two light chain clones LC1 & LC2, respectively.

FIG. 3B is a photograph of a gel depicting western blot analysis of expression of light chain of factor VIII: C in *Pichia pastoris* GS115, wherein lanes 2-4 correspond to the following uninduced cultures; heavy chain clone HC1, and two light chain clones LC1 & LC2, respectively, and further wherein lanes 5-7 correspond to the following cultures induced for 90 hrs; heavy chain clone HC1, and two light chain clones LC1 & LC2, respectively.

DETAILED DESCRIPTION OF THE PREFERRED EMBODIMENTS

Figure 1A:
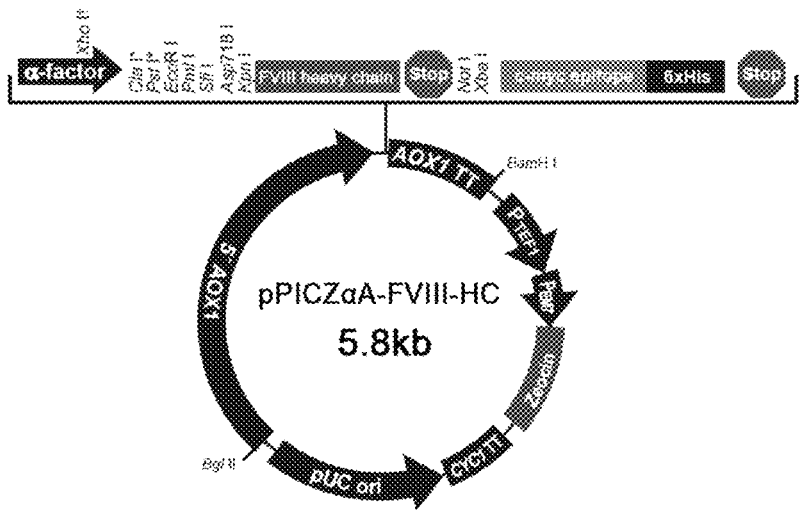
FIG. 1A is a graphical representation depicting a heavy chain construct of Factor VIII: C in *Pichia* expression vector pPICZαA.

The present disclosure relates to a DNA construct comprising a polynucleotide sequence having at least 95% sequence identity to a sequence as set forth in SEQ ID NO. 1.

In an embodiment of the present disclosure, said sequence encodes a polypeptide corresponding to Factor VIII heavy chain.

The present invention further relates to a DNA construct comprising a polynucleotide sequence having at least 95% sequence identity to a sequence as set forth in SEQ ID NO. 3.

In an embodiment of the present disclosure, said sequence encodes a polypeptide corresponding to Factor VIII light chain.

The present invention further relates to a vector comprising a polynucleotide sequence as set forth in SEQ ID NO. 1, SEQ ID NO. 3 or a combination thereof.

The present invention further relates to a vector comprising polynucleotide sequence as set forth in SEQ ID NO. 1.

In an embodiment of the present disclosure, the vector comprising SEQ ID NO. 1 has been deposited under accession number MTCC 5854.

The present invention further relates to a vector comprising a polynucleotide sequence as set forth in SEQ ID NO. 3.

In an embodiment of the present disclosure, the vector comprising SEQ ID NO. 3 has been deposited under accession number MTCC 5853.

The present invention further relates to a vector comprising a polynucleotide sequence as set forth in SEQ ID NO. 1 and SEQ ID NO. 3.

The present invention further relates to a host cell comprising a polynucleotide sequence of SEQ ID NO. 1, SEQ ID NO. 3 or a combination thereof The present invention further relates to a host cell comprising the vector comprising a polynucleotide sequence as set forth in SEQ ID NO. 1.

The present invention further relates to a host cell comprising the vector comprising a polynucleotide sequence as set forth in SEQ ID NO. 3.

The present invention further relates to a host cell comprising the vector comprising a polynucleotide sequence as set forth in SEQ ID NO. 1 and SEQ ID NO. 3.

The present invention further relates to a process for obtaining heavy chain peptide or light chain peptide of recombinant Factor VIII protein or a combination thereof, said method comprising the act of culturing cells of non-filamentous fungi comprising a nucleotide sequence corresponding to the peptide to obtain said peptide.

The present invention further relates to a process for obtaining a heavy chain peptide of recombinant Factor VIII protein, said method comprising the act of culturing cells of non-filamentous fungi comprising a nucleotide sequence corresponding to the heavy chain peptide.

The present invention further relates to a process for obtaining a light chain peptide of recombinant Factor VIII protein, said method comprising the act of culturing cells of non-filamentous fungi comprising a nucleotide sequence corresponding to the light chain peptide.

In an embodiment of the present invention, the heavy chain peptide corresponds to the polynucleotide sequence of SEQ ID NO. 1, the light chain peptide corresponds to the polynucleotide sequence of SEQ ID NO. 3 and the non-filamentous fungi is selected from a group comprising, but not limited to, *Pichia pastoris, Saccharomyces cerevisiae* and *Hansenula polymorpha*, preferably *Pichia pastoris*.

The present invention further relates to a process for obtaining a recombinant factor VIII protein, said process comprising acts of:
a. introducing the polynucleotide sequence of SEQ ID NO. 1 or the polynucleotide sequence of SEQ ID NO. 1 or a combination thereof into a host cell to obtain corresponding polypeptides individually or in combination; or
b. introducing the vector comprising polynucleotide sequence of SEQ ID NO. 1, SEQ ID NO. 3 or a combination thereof into a host cell to obtain corresponding polypeptides individually or in combination; and
c. reconstituting the polypeptides produced by step (a) or (b) to obtain the recombinant Factor VIII protein.

In an embodiment of the present invention, the host cell is a non-filamentous fungi.

In an embodiment of the present invention, the non-filamentous fungi is selected from a group comprising, but not limited to, *Pichia pastoris, Saccharomyces cerevisiae* and *Hansenula polymorpha*, preferably *Pichia pastoris*.

In an embodiment of the present invention, the reconstitution is carried out in the presence of divalent metal ions.

In an embodiment of the present invention, the reconstitution is carried out in the presence of $Ca^{++}$ or $Cu^{++}$ ions or a combination thereof.

In an embodiment of the present invention, the process further comprise purification of said polypeptides.

In an embodiment of the present disclosure, the purification of said polypeptides is carried out individually or in combination.

In an embodiment of the present invention, the purification of said polypeptides is carried out by chromatographic techniques.

In an embodiment of the present invention, the purification of said polypeptides is carried out by IMAC (Immobilized Metal-ion Affinity Chromatography) and HLAC (Histidine Ligand Affinity Chromatography.

In an embodiment of the present invention, the purification of heavy chain peptide is carried out by IMAC.

In an embodiment of the present invention, the purification of heavy chain peptide involves elution at a pH ranging from 4.5 to 5.8, preferably 5.0.

In an embodiment of the present invention, the purification of light chain peptide is carried out by HLAC.

In an embodiment of the present invention, the purification of light chain peptide involves elution at a pH ranging from 6.5 to 7.5, preferably 7.0.

In an embodiment of the present invention, the recombinant factor VIII obtained by the process shows better or improved activity.

In an embodiment of the present invention, the process of the present disclosure avoids the difficulty in expressing full length recombinant Factor VIII.

The present invention further relates to a process for obtaining recombinant factor VIII protein, said process comprising acts of:
a. introducing the polynucleotide sequence of SEQ ID NO. 1 into a first host cell to obtain a corresponding polypeptide of SEQ ID NO. 2;
b. introducing the polynucleotide sequence of SEQ ID NO. 3 into a second host cell to obtain a corresponding polypeptide of SEQ ID NO. 4;
c. optionally introducing the vector comprising polynucleotide sequence of SEQ ID NO. 1 into a first host cell to obtain a corresponding polypeptide of SEQ ID NO. 2;
d. optionally introducing the vector comprising polynucleotide sequence of SEQ ID NO. 3 into a second host cell to obtain a corresponding polypeptide of SEQ ID NO. 4; and
e. reconstituting the polypeptides produced by step (a) and (b) or (c) and (d) to obtain the recombinant Factor VIII protein.

In an embodiment of the present invention, the host cell is a non-filamentous fungi.

In an embodiment of the present invention, the non-filamentous fungi is selected from a group comprising, but not limited to, *Pichia pastoris, Saccharomyces cerevisiae* and *Hansenula polymorpha*, preferably *Pichia pastoris*.

In an embodiment of the present invention, the reconstitution is carried out in the presence of divalent metal ions.

In an embodiment of the present invention, the reconstitution is carried out in the presence of $Ca^{++}$ or $Cu^{++}$ ions or a combination thereof.

In an embodiment of the present invention, the process further comprise purification of said polypeptides.

In an embodiment of the present disclosure, the purification of said polypeptides is carried out individually or in combination.

In an embodiment of the present invention, the purification of said polypeptides is carried out by chromatographic techniques.

In an embodiment of the present invention, the purification of said polypeptides is carried out by IMAC (Immobilized Metal-ion Affinity Chromatography) and HLAC (Histidine Ligand Affinity Chromatography.

In an embodiment of the present invention, the purification of heavy chain peptide is carried out by IMAC.

In an embodiment of the present invention, the purification of heavy chain peptide involves elution at a pH ranging from 4.5 to 5.8, preferably 5.0.

In an embodiment of the present invention, the purification of light chain peptide is carried out by HLAC.

In an embodiment of the present invention, the purification of light chain peptide involves elution at a pH ranging from 6.5 to 7.5, preferably 7.0.

In an embodiment of the present invention, the recombinant factor VIII obtained by the process shows better or improved activity.

In an embodiment of the present invention, the process of the present disclosure avoids the difficulty in expressing full length recombinant Factor VIII.

The present invention relates to a process for enhancing activity of recombinant factor VIII protein, said process comprising acts of:
a. introducing the polynucleotide sequence of SEQ ID NO. 1 or the polynucleotide sequence of SEQ ID NO. 3 or a combination thereof into a host cell to obtain corresponding polypeptides individually or in combination; or
b. introducing the vector comprising polynucleotide sequence of SEQ ID NO. 1 or the polynucleotide sequence of SEQ ID NO. 3 or a combination thereof into a host cell to obtain corresponding polypeptides individually or in combination; and c. reconstituting the polypeptides produced by step (a) or (b) to obtain the recombinant Factor VIII protein showing enhanced activity.

As used herein, the following sequences are set forth and followed in the present disclosure—

SEQ ID NO. 1: Polynucleotide Sequence coding for the Heavy chain of BDD-Factor VIII.

SEQ ID NO. 2: Amino acid sequence of the Heavy chain of BDD-Factor VIII encoded by polynucleotide sequence of SEQ ID NO:1.

SEQ ID NO. 3: Polynucleotide Sequence coding for the Light chain of BDD-Factor VIII.

SEQ ID NO. 4: Amino acid sequence of the Light chain of BDD-Factor VIII encoded by polynucleotide sequence of SEQ ID NO:3.

In an embodiment, the present disclosure relates to polynucleotide sequences having at least 95% sequence identity to the sequence as set forth in SEQ ID NO. 1.

In an embodiment, the present disclosure relates to polynucleotide sequences having at least 95% sequence identity to the sequence as set forth in SEQ ID NO. 3.

Throughout the disclosure, the heavy chain is referred interchangeably as "HC", "heavy chain" and "heavy chain peptide", the light chain is referred interchangeably as "LC", "light chain" and "light chain peptide" and the recombinant factor VIII is referred interchangeably as "BDD-factor VIII", "recombinant factor VIII", "Factor VIII:C" and "Factor VIII"

The vector pPICZαA-FVIII-HC comprising heavy chain (SEQ ID No:1) of BDD-Factor VIII has been deposited with the International Depository "The Microbial Type Culture Collection and Gene Bank (MTCC)" and has been accorded the accession number MTCC 5854.

The vector pPICZαA-FVIII-LC comprising light chain (SEQ ID No:3) of BDD-Factor VIII has been deposited with the International Depository "The Microbial Type Culture Collection and Gene Bank (MTCC)" and has been accorded the accession number MTCC 5853.

In an embodiment, the present disclosure describes the production of recombinant Factor VIII using non-filamentous methylotropic yeast, particularly *Pichia pastoris*. In this method, the heavy and light chains of Factor VIII have been independently expressed using respective constructs in *Pichia pastoris* strain GS115. Subsequently, the expressed heavy and light chains are purified to near-homogenity using Immobilized Metal-ion Affinity Chromatography [IMAC] and Histidine Ligand Affinity Chromatography [HLAC], respectively. Functional Factor VIII: C is reconstituted from the recombinantly expressed individual chains in vitro, assayed for its specific activity by one-stage clotting assay and chromogenic assay and the reconstituted Factor VIII: C is shown to be functional and highly active. The method also avoids the difficulty in expressing full length recombinant Factor VIII.

Additional embodiments and features of the present disclosure will be apparent to one of ordinary skill in art based upon description provided herein. However, the examples and the figures should not be construed to limit the scope of the present disclosure.

EXAMPLE 1

Materials Used

The vector pcDNA3.1 containing the B-domain deleted factor VIII gene is obtained. All primers for PCR amplification are synthesised by Sigma-Aldrich Ltd. (Bangalore, India). The expression vector pPICZαA and *Pichia pastoris* strain GS115 are obtained from commercially available kits.

Rabbit anti-A1 and anti-C2 antisera for the detection of heavy and light chains respectively were generated in-house.

Growth media, buffers for chromatographic runs, and reagents are prepared using chemicals of analytical grade either from Sigma-Aldrich (Bangalore, India) or HiMedia (Bangalore, India).

Preparation of Expression Constructs for Heavy & Light Chains of Factor VIII: C

The region corresponding to the heavy chain of factor VIII: C molecule (2220bp long comprising of the A1 and A2 domains) are amplified using the forward primer (SEQ. ID NO: 5 (5'GTGGCCCAGCCGGCCAGCCACCAGAAGA-TAC3')) incorporating SfiI site and reverse primer (SEQ. ID NO: 6 (5'AATGCGGCCGCTCATCTTGGTTCAAT3')) incorporating NotI site. The amplified cDNA fragment is restriction digested and cloned into the yeast expression vector pPICZαA and transformed into the host *E. coli* strains. The *E. coli* transformants are screened with Zeocin.

The 2055bp Light chain gene is amplified by PCR using the forward primer (SEQ. ID NO. 7 (5'AAGGTAC-CGAAATAACTCGTACTACTCTTC3')) incorporating KpnI restriction site and reverse primer SEQ. ID NO: 8 (5'AAG CGGCCGCAGTAGAGGTCCTGTGCC-3')) incorporating NotI restriction site. The amplified gene is cloned into pPICZαA, transformed into *E. coli* and screened with Zeocin resistance.

Results

Figure 1B:
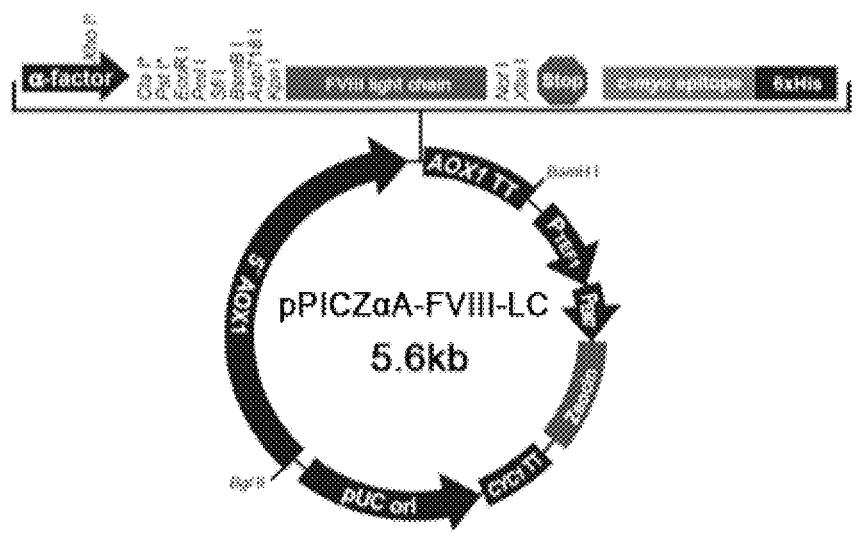
FIG. 1B is a graphical representation depicting a light chain construct of Factor VIII: C in *Pichia* expression vector pPICZαA.

The cDNA corresponding to the Heavy chain and Light chain of Factor VIII: C are independently cloned into the yeast expression vector pPICZαA, and the respective constructs are confirmed to have proper integration of the insert in the correct reading frame by DNA sequencing of the termini using AOX1-specific primers. The expression constructs are depicted in FIGS. 1A and 1B for the heavy chain and light chain, respectively.

EXAMPLE 2

Transformation of Expression Constructs in *Pichia pastoris* GS115

Competent *Pichia pastoris* cells are prepared as per the condensed protocol by Lin-Cereghino et. al. (2005). Transformation of 5-10 μg of PmeI linearised plasmid pPICZαA-FVIII-HC/pPICZαA-FVIII-LC into competent *P. pastoris* GS115 is carried out by electroporation using Eppendorf Multiporator (Eppendorf AG, Germany) under the 'bacteria and yeast' module, as per manufacturer's instructions. Electroporation is carried out in 2 mm electroporation cuvettes at 1,500V for 5 minutes with 6000 resistance and 10 μF capacitance. Screening for transformants is achieved using antibiotic Zeocin™ at concentrations upto 1 mg/ml.

Results

Competent *Pichia pastoris* GS115 cells are transformed with the construct containing the appropriate insert. After 3-4 days of incubation on Yeast Extract Peptone Dextrose (YPD) plates, the cells growing on plates with zeocin concentrations up to 1 mg/ml are selected, screened for their methanol utilization phenotype and confirmed for the genomic integration of DNA by PCR analysis.

EXAMPLE 3

Protein Expression

Expression of individual chains of Factor VIII: C is carried out as described in the *Pichia* Expression Kit manual version E (Invitrogen, USA). The transformed cells are grown in buffered minimal complex glycerol media (BMGY, 100 mM potassium phosphate buffer at pH 6.0, 13.4 g/L YNB, $4 \times 10^{-4}$ g/L biotin, 10 g/L glycerol) for 24 hours after which they are transferred to buffered minimal complex methanol media (BMMY, 100 mM potassium phosphate buffer at pH 6.0, 13.4 g/L YNB, $4 \times 10^{-4}$ g/L biotin, 0.5% methanol) and induced for a period of 90-120 hours with methanol being added at 0.5%-1% every 24 hours. In order to analyze the expression levels, samples are drawn from each culture at various time points and concentrated by Trichloro Acetic Acid (TCA) precipitation, after which they are subjected to 10% SDS-PAGE under reducing conditions followed by western blotting on to a nitrocellulose membrane.

SDS-PAGE and Western Blotting Analysis

Western blotting is performed on expressed samples to confirm the presence of factor VIII heavy/light chain. About 5 µg of protein sample is loaded on each well of a 10% polyacrylamide gel, and SDS-PAGE is performed to separate them. After electrophoresis, the proteins from the polyacrylamide gel are transferred to a nitrocellulose membrane using Mini Trans-Blot Cell (BIO-RAD, India). Towbin transfer buffer (25 mM Tris, 200 mM glycine, 0.01% SDS, 20% methanol, pH 8.3) is used to carry out the transfer from the polyacrylamide gel to the nitrocellulose membrane (Towbin et al., 1979), at 90V for 90 mins at 4° C. The membrane is washed with PBST (Phosphate Buffered Saline with 0.1% Tween-20), blocked with a blocking buffer (PBST with 5% skimmed milk powder) overnight at 4° C. After blocking, the membrane is incubated with primary antibody (rabbit anti-$A_1$ or anti-$C_2$ antiserum) at room temperature for one hour. The membrane is washed 3 times with PBST solution after which it is incubated with secondary antibody (goat anti-rabbit IgG, HRP conjugated) at room temperature for 1 hour. The membrane is then washed thrice with PBST. The membrane is developed by enhanced chemiluminescence (ECL) using Super Signal West Pico Chemiluminescent Substrate (Pierce, India) on to an X-ray film (Kodak India Ltd., Chennai).

Results

Expression of FVIII: C heavy chain is achieved by induction of heavy chain containing *Pichia pastoris* GS115 clones with 0.5%-1% methanol as explained above. The FVIII: C heavy chain expression construct has an alpha-mating factor signal peptide which helps to secrete the heterologous protein into the culture medium. The recombinantly expressed FVIII: C heavy chain protein is observed in the culture medium. The cultures are harvested after 90 hours of induction with intermittent replenishment of methanol at 0.5% every 24 hrs. In order to analyze the expression levels, samples are drawn from each culture at various time points and concentrated by Trichloro Acetic Acid (TCA) precipitation, after which they are subjected to 10% SDS-PAGE under reducing conditions followed by western blotting on to nitrocellulose membrane. The rabbit anti-$A_1$ antiserum is used as primary antibody in the blot, following which the membrane is probed with goat anti-rabbit IgG (HRP-conjugated) as secondary antibody. The membrane is then developed by enhanced chemiluminescence. From FIG. 2, it is observed that a distinct band at ~180 kDa is present only in the heavy chain clone $HC_1$ (indicated by an arrow), whereas other bands are observed in all lanes including the vector control suggestive of non-specific nature of anti-HC antibody. Despite this non-specificity, the fact that the antibody is able to recognize this 180 KDa protein in case of heavy chain clone $HC_1$ distinguishes this clone from the others.

Expression of light chain of Factor VIII: C is carried out similar to the heavy chain expression of *Pichia pastoris* GS115. The cultures are harvested after 90 hours-120 hours of induction. For analyzing expression levels, 1 mL samples drawn at various time points are concentrated by precipitating the proteins using TCA. They are then subjected to 10% SDS-PAGE under reducing conditions followed by western blotting on to nitrocellulose membrane. Antisera (prepared using *E. coli* expressed C2 domain of FVIII: C as antigen) is used as primary antibody in the western blot analysis. As seen in FIG. 3A, both clones ($LC_1$ and $LC_2$ in lanes 6 and 7) exhibited around 97 kDa, which is the expected band, higher than the predicted 80 kDa (owing to the two glycosylation sites) with slight difference in intensity upon induction. The heavy chain expressing clone $HC_1$ is taken as a negative control where signal corresponding to the expected molecular weight of the light chain (lane 5) is not observed. Also, the lanes corresponding to uninduced samples (lanes 2, 3 and 4) do not show any signal. This data indicates the successful expression of light chain of FVIII: C in *Pichia pastoris*.

EXAMPLE 4

Purification of FVIII: C Heavy Chain and Light Chain Expressed in *Pichia pastoris* Broth Purification of heavy chain of factor VIII: C from the heavy chain expressing *Pichia pastoris* clone is carried out using Immobilized Metal-ion Affinity Chromatography (IMAC). The results are provided in FIG. 4A.

Figure 5A:
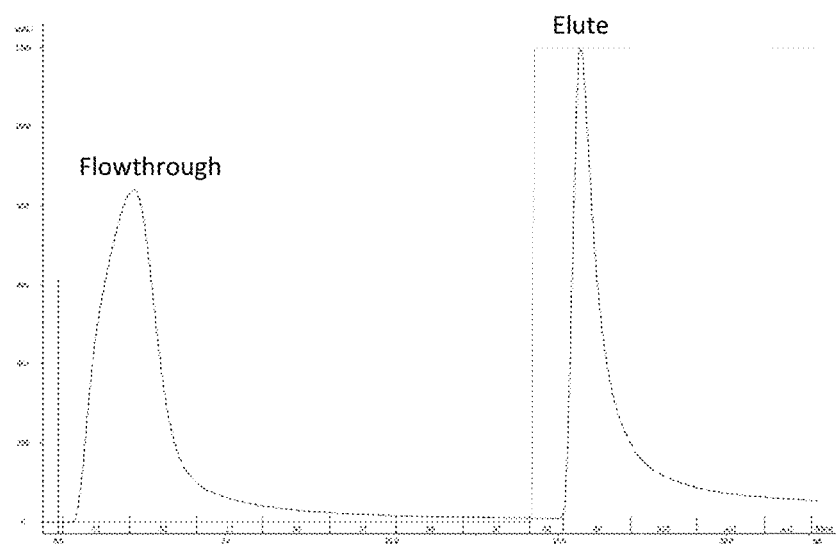
FIG. 5A is a graphical representation of purification results of a light chain FVIII: C in *Pichia pastoris* using Histidine Ligand Affinity Chromotography (HLAC)

For the purification of the *Pichia* expressed recombinant light chain of Factor VIII: C, Histidine Ligand Affinity Chromatography (HLAC) is employed. The results are provided in FIG. 5A.

Results

Immobilized Metal-ion Affinity Chromatography (IMAC) is employed to purify the expressed heavy chain of FVIII: C in *Pichia pastoris* clone $HC_1$. The integrity of the purified protein is analyzed over SDS-PAGE and western blotting. While sharp peaks are observed during each elution step (FIG. 4A), it is observed that the heavy chain protein is obtained to near homogeneity upon elution at pH 5.0. When analyzed by SDS-PAGE and western blotting under non-reducing conditions (FIGS. 4B & 4C), the heavy chain protein is observed to aggregate as a dimer, which breaks down upon reduction with DTT showing a clear band at the expected 90 kDa molecular weight (FIG. 4D). Although the lanes corresponding to elution at pH 4 and pH 6 shows a band (FIG. 4D), it is not as prominent and hence it is desirable to elute the heavy chain at a pH ranging from 4.5 to 5.8, preferably 5.

Figure 4A:
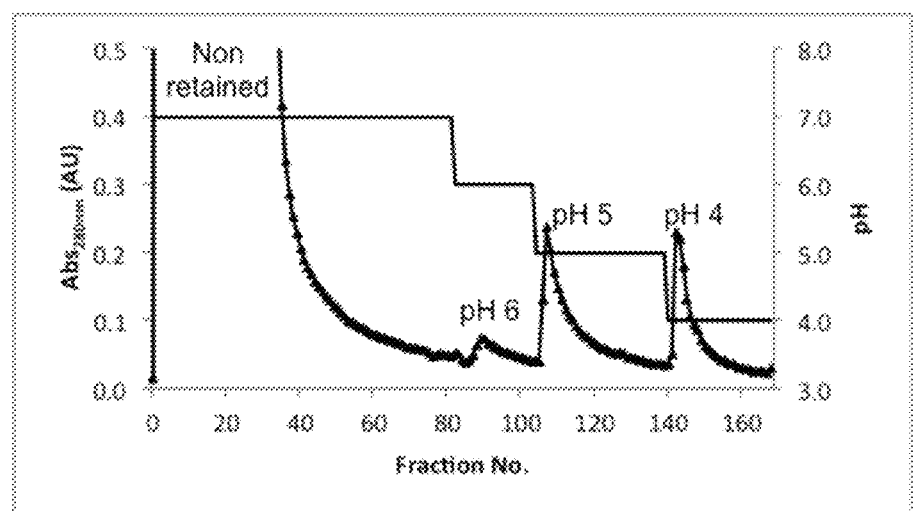
FIG. 4A is a graphical representation depicting purification results of heavy chain FVIII: C using Immobilized Metal-ion Affinity Chromatography (IMAC) under non-reducing conditions.
Figure 4B:
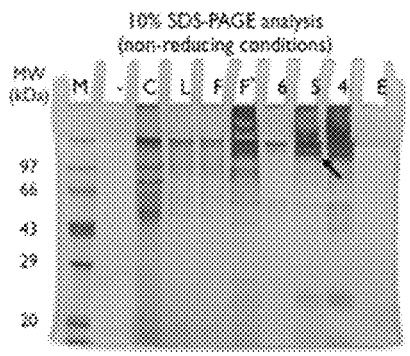
FIG. 4B is a photograph of a gel depicting an SDS-PAGE analysis of a purified heavy chain of FVIII: C under non-reducing conditions.
Figure 4C:
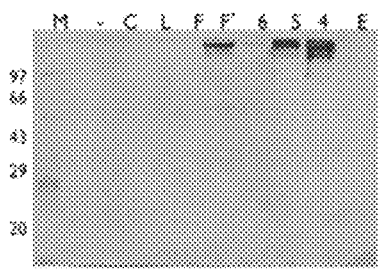
FIG. 4C is a photograph of a gel depicting a western blot analysis of a purified heavy chain of FVIII: C under non-reducing conditions.
Figure 4D:
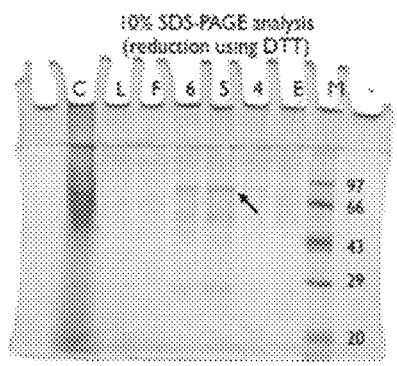
FIG. 4D is a photograph of a gel depicting an SDS-PAGE analysis of a purified heavy chain of FVIII: C under reducing conditions.

With reference to FIGS. 4A-4C, a chromatogram analysis is shown (FIG. 4A), an SDS-PAGE analysis is shown (FIG. 4B) and a western blot analysis is shown (FIG. 4C). The analyses shown in FIGS. 4A-4C are shown under non-reducing conditions. With reference to FIG. 4D, an SDS-PAGE analysis under reducing conditions is shown. For FIGS. 4A-4D, the lanes correspond to control *Pichia* broth which doesn't express heavy chain (−), medium range protein marker (M), vector control broth (C), load (L), unbound fractions (F, F'), bound fractions eluted at pH 6.0/5.0/4.0 (6,5,4) and EDTA-eluted fraction (E).

Histidine Ligand Affinity Chromatography (HLAC) is employed to purify the expressed light chain of FVIII: C in *Pichia pastoris*. It is observed that the light chain protein is obtained to near homogeneity upon elution at pH 7.0. The load, flow through and eluted fractions of the chromatography experiment (FIG. 5A) are analyzed over 10% SDS-PAGE under non-reducing conditions. Upon SDS-PAGE under non-reducing conditions, a band corresponding to the light chain protein (FIG. 5B) is observed in the eluted fraction. The eluted fraction shows a band above the expected 80 kDa, more specifically around 97 kDa, as in the case of the expression study (FIGS. 3A & 3B), but the same is confirmed by western and ELISA (FIG. 5C) analysis using anti-C2 antibody. This increase in the theoretically predicted molecular weight is attributed to glycosylation on the light chain residues.

Figure 5B:
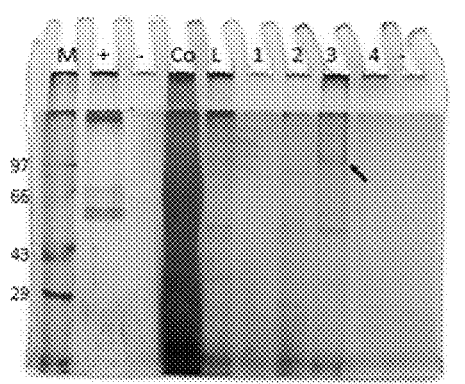
FIG. 5B is a photograph of a gel depicting a 10% SDS-PAGE analysis of light chain FVIII: C of FIG. 5A under non-reducing conditions.
Figure 5C:
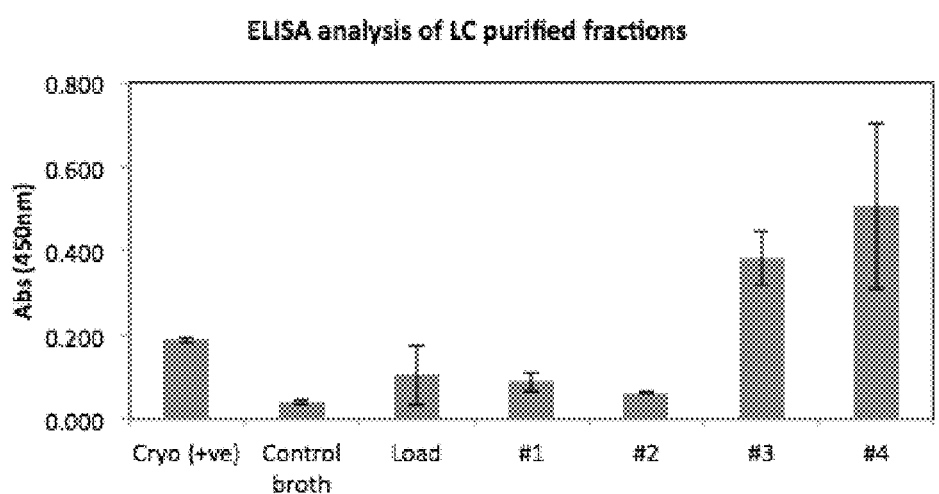
FIG. 5C is a graphical representation of an Enzyme-Linked Immuno Assay (ELISA) analysis of light chain FVIII: C purified fractions.

For FIG. 5B, a Load (L), Unbound fractions (1, 2) and Eluted fractions (3, 4) are analyzed, in addition to a blank (−), commercially purified Factor VIII: C (+, used as positive control) and a control Pichia broth (Co−) not expressing the light chain protein.

EXAMPLE 5

Reconstitution of Factor VIII: C from Individual Chains Expressed in Pichia pastoris GS115 and Activity Results Full length B-domain deleted Factor VIII: C is regenerated from individual heavy & light chains expressed in Pichia pastoris expression system. Equimolar concentrations of heavy and light chains are reconstituted in 20 mM HEPES, pH 7.0-7.4 containing 0.3M KCl, 0.01% Tween-20, 0.01% BSA, 25 mM CaCl$_2$ and 0.5 µM Cu$^{++}$ and incubated at 20° C.-23° C. for 4 hours-6 hours. Following this, their specific activity is determined by one-stage clotting assay using FVIII-depleted plasma (Siemens Healthcare Diagnostics, USA) over IL ACL 10000 coagulation analyzer (Instrumentation Laboratory, Italy). The One stage clotting assay is performed as follows—

Factor VIII-depleted plasma is dissolved in distilled or deionized water. Before use, it is allowed to stand for at least 15 minutes at 15 to 25° C., and then mixed carefully without foam formation. The reconstituted recombinant Factor VIII: C sample are added to FVIII deficient plasma. APTT reagents are used according to the manufacturer's instructions. 0.025M of CaCl$_2$ is added to the mixture. The mixture is incubated at 37° C. for 2 minutes and the reading is taken in an automated coagulation analyzer. Normal clotting time is 30-40 seconds.

Results

Reconstitution of Pichia expressed Heavy Chain & Light Chain is performed as described above. The activity results and a comparative study with the prior art results are provided in Table 1.

TABLE 1

One stage clotting assay results

| Name of the Protein | Specific Activity[IU/mg] |
|---|---|
| Reconstituted recombinant FVIII: C (Heavy chain and Light chain derived from bacculovirus insect cell expression system) | 0.0285 |
| Reconstituted recombinant FVIII: C (Heavy chain and Light chain derived from Pichia pastoris expression system) | 132 |

TABLE 2

Chromogenic assay results

| Name of the Protein | Specific Activity[IU/mg] |
|---|---|
| Reconstituted recombinant FVIII: C (Heavy chain and Light chain derived from Pichia pastoris expression system) | 7665 |

Conclusion

The present disclosure discloses successful independent expression of heavy and light chains of Factor VIII: C by the Pichia pastoris expression system. The expressed heavy chain and the light chain are purified, reconstituted in presence of Calcium ions to obtain the full-length recombinant Factor VIII: C and the activity of the full-length recombinant Factor VIII: C is studied. The activity exhibited by the reconstituted Factor VIII molecule of the present disclosure shows a significant improvement when compared to the reconstituted Factor VIII molecules of the prior art, thus proving Pichia pastoris expression system to be an effective expression system for the production of potential recombinant Factor VIII: C protein by making use of the process of the present disclosure.

Advantages:

The recombinant factor VIII expressed in Pichia is more important when compared to the plasma-derived factor VIII due to the following reasons:

- Its ease in handling, and its GRAS (Generally Regarded As Safe) microbe status,
- The ability to grow to high cell densities and enhance the production levels when scaled-up to a bioreactor.
- The strain of Pichia pastoris GS115 used in the present disclosure, has a glycosylation mechanism closely resembling higher eukaryotes thereby reducing the risk of immune rejection,
- The possibility of glyco-engineering this strain to generate more "human like" glycosylation poses a huge advantage,
- The secretion of protein into the media by Pichia pastoris facilitates purification, which is a major advantage when we take this product to industrial levels of production,
- The Pichia pastoris expression system secretes low amounts of host proteins, making purification of target protein easier.

More so, expressing heavy chain and light chain of Recombinant factor VIII individually and reconstituting according to the present disclosure avoids the difficulty in expressing full length recombinant Factor VIII.

We claim:

1. A process for obtaining a recombinant Factor VIII protein, said process comprising the steps of:
   a. transforming an isolated host cell with a polynucleotide comprising the nucleotide sequence of SEQ ID NO: 1, which encodes a Factor VIII heavy chain polypeptide, and a polynucleotide comprising the nucleotide sequence of SEQ ID NO: 3, which encodes a Factor VIII light chain polypeptide, and expressing each of the polynucleotides to produce individual Factor VIII heavy chain and light chain polypeptides; and
   b. reconstituting the Factor VIII heavy chain and light chain polypeptides produced by step (a) to obtain the recombinant Factor VIII protein.

2. The process as claimed in claim 1, wherein the host cell is a nonfilamentous fungi selected from the group consisting of *Pichia pastoris, Saccharomyces cerevisiae* and *Hansenula polymorpha*.

3. The process as claimed in claim 1, wherein the reconstitution step (b) is carried out in the presence of divalent metal ions, wherein the divalent metal ions include one of a $Ca^{++}$ion, a $Cu^{++}$ion, and a combination thereof.

4. The process as claimed in claim 1, wherein the process further includes a step of purifying the Factor VIII heavy chain and light chain polypeptides prior to the reconstitution step (b).

5. The process as claimed in claim 4, wherein the step of purifying the Factor VIII heavy chain and light chain polypeptides includes purifying the polypeptides using a chromatographic technique, and further wherein the chromatographic technique includes one of an Immobilized Metal-ion Affinity Chromatography technique, and a Histidine Ligand Affinity Chromatography technique.

6. The process as claimed in claim 1, wherein each of the polynucleotides is present within a polynucleotide vector.

7. A DNA construct comprising the nucleotide sequence of SEQ ID NO: 1, which encodes a Factor VIII heavy chain polypeptide.

8. A DNA construct comprising the nucleotide sequence of SEQ ID NO: 3, which encodes a Factor VIII light chain polypeptide.

9. A process for obtaining a Factor VIII heavy chain polypeptide, a Factor VIII light chain polypeptide, or a combination thereof, said process comprising the steps of:
   a. culturing cells of non-filamentous fungi comprising:
      (i) a polynucleotide which comprises the nucleotide sequence of SEQ ID NO: 1 and which encodes a Factor VIII heavy chain polypeptide,
      (ii) a polynucleotide which comprises the nucleotide sequence of SEQ ID NO: 3 and which encodes a Factor VIII light chain polypeptide, or
      (iii) a combination of the polynucleotides of (i) and (ii), and
   b. expressing the polynucleotide of (i) or (ii) or the combination of polynucleotides of (iii) to obtain said polypeptide or combination of polypeptides.

10. The process as claimed in claim 9, wherein the non-filamentous fungi is selected from the group consisting of *Pichia pastoris, Saccharomyces cerevisiae* and *Hansenula polymorpha*.

11. A vector comprising a polynucleotide which comprises the nucleotide sequence as set forth in SEQ ID NO: 1, SEQ ID NO: 3, or a combination of the nucleotide sequences of SEQ ID NO: 1 and SEQ ID NO: 3.

12. An isolated host cell comprising the vector as claimed in claim 11.

* * * * *

SEQUENCE LISTING

<160> NUMBER OF SEQ ID NOS: 8

<210> SEQ ID NO 1
<211> LENGTH: 2247
<212> TYPE: DNA
<213> ORGANISM: Homo sapiens

```
<220> FEATURE:
<221> NAME/KEY: gene
<222> LOCATION: (1)..(2247)

<400> SEQUENCE: 1
```

| | | | | | |
|---|---|---|---|---|---|
| gaattcacgt | ggcccagccg | gccagccacc | agaagatact | acctgggtgc | agtggaactg | 60 |
| tcatgggact | atatgcaaag | tgatctcggt | gagctgcctg | tggacgcaag | atttcctcct | 120 |
| agagtgccaa | aatcttttcc | attcaacacc | tcagtcgtgt | acaaaaagac | tctgtttgta | 180 |
| gaattcacgg | atcacctttt | caacatcgct | aagccaaggc | caccctggat | gggtctgcta | 240 |
| ggtcctacca | tccaggctga | ggtttatgat | acagtggtca | ttacacttaa | gaacatggct | 300 |
| tcccatcctg | tcagtcttca | tgctgttggt | gtatcctact | ggaaagcttc | tgagggagct | 360 |
| gaatatgatg | atcagaccag | tcaaagggag | aaagaagatg | ataaagtctt | ccctggtgga | 420 |
| agccatacat | atgtctggca | ggtcctgaaa | gagaatggtc | caatggcctc | tgacccactg | 480 |
| tgccttacct | actcatatct | ttctcatgtg | gacctggtaa | agacttgaa | ttcaggcctc | 540 |
| attggagccc | tactagtatg | tagagaaggg | agtctggcca | aggaaaagac | acagaccttg | 600 |
| cacaaattta | tactactttt | tgctgtattt | gatgaaggga | aaagttggca | ctcagaaaca | 660 |
| aagaactcct | tgatgcagga | tagggatgct | gcatctgctc | gggcctggcc | taaaatgcac | 720 |
| acagtcaatg | gttatgtaaa | caggtctctg | ccaggtctga | ttggatgcca | caggaaatca | 780 |
| gtctattggc | atgtgattgg | aatgggcacc | actcctgaag | tgcactcaat | attcctcgaa | 840 |
| ggtcacacat | tcttgtgag | aaccatcgc | caggcgtcct | ggaaatctc | gccaataact | 900 |
| ttccttactg | ctcaaacact | cttgatggac | cttggacagt | ttctactgtt | ttgtcatatc | 960 |
| tcttcccacc | aacatgatgg | catggaagct | tatgtcaaag | tagacagctg | tccagaggaa | 1020 |
| ccccaactac | gaatgaaaaa | taatgaagaa | gcggaagact | atgatgatga | tcttactgat | 1080 |
| tctgaaatgg | atgtggtcag | gtttgatgat | gacaactctc | cttcctttat | ccaaattcgc | 1140 |
| tcagttgcca | agaagcatcc | taaaacttgg | gtacattaca | ttgctgctga | agaggaggac | 1200 |
| tgggactatg | ctcccttagt | cctcgccccc | gatgacagaa | gttataaaag | tcaatatttg | 1260 |
| aacaatggcc | ctcagcggat | tggtaggaag | tacaaaaaag | tccgatttat | ggcatacaca | 1320 |
| gatgaaacct | ttaagactcg | tgaagctatt | cagcatgaat | caggaatctt | gggaccttta | 1380 |
| ctttatgggg | aagttggaga | cacactgttg | attatattta | agaatcaagc | aagcagacca | 1440 |
| tataacatct | accctcacgg | aatcactgat | gtccgtcctt | tgtattcaag | gagattacca | 1500 |
| aaaggtgtaa | acatttgaa | ggattttcca | attctgccag | agaaatatt | caaatataaa | 1560 |
| tggacagtga | ctgtagaaga | tgggccaact | aaatcagatc | ctcggtgcct | gacccgctat | 1620 |
| tactctagtt | tcgttaatat | ggagagagat | ctagcttcag | gactcattgg | ccctctcctc | 1680 |
| atctgctaca | aagaatctgt | agatcaaaga | ggaaaccaga | taatgtcaga | caagaggaat | 1740 |
| gtcatcctgt | tttctgtatt | tgatgagaac | cgaagctggt | acctcacaga | gaatatacaa | 1800 |
| cgctttctcc | ccaatccagc | tggagtgcag | cttgaggatc | cagagttcca | agcctccaac | 1860 |
| atcatgcaca | gcatcaatgg | ctatgttttt | gatagtttgc | agttgtcagt | tgtttgcat | 1920 |
| gaggtggcat | actggtacat | tctaagcatt | ggagcacaga | ctgacttcct | ttctgtcttc | 1980 |
| ttctctggat | ataccttcaa | acacaaaatg | gtctatgaag | acacactcac | cctattccca | 2040 |
| ttctcaggag | aaactgtctt | catgtcgatg | gaaaacccag | gtctatggat | ctggggtgc | 2100 |
| cacaactcag | actttcggaa | cagaggcatg | accgccttac | tgaaggtttc | tagttgtgac | 2160 |
| aagaacactg | gtgattatta | cgaggacagt | tatgaagata | tttcagcata | cttgctgagt | 2220 | aaaaacaatg ccattgaacc aagatga                                           2247

<210> SEQ ID NO 2
<211> LENGTH: 748
<212> TYPE: PRT
<213> ORGANISM: Homo sapiens
<220> FEATURE:
<221> NAME/KEY: PEPTIDE
<222> LOCATION: (1)..(748)

<400> SEQUENCE: 2

Glu Phe Thr Trp Pro Ser Arg Pro Ala Thr Arg Arg Tyr Tyr Leu Gly
1               5                   10                  15

Ala Val Glu Leu Ser Trp Asp Tyr Met Gln Ser Asp Leu Gly Glu Leu
            20                  25                  30

Pro Val Asp Ala Arg Phe Pro Pro Arg Val Pro Lys Ser Phe Pro Phe
        35                  40                  45

Asn Thr Ser Val Val Tyr Lys Lys Thr Leu Phe Val Glu Phe Thr Asp
    50                  55                  60

His Leu Phe Asn Ile Ala Lys Pro Arg Pro Trp Met Gly Leu Leu
65              70                  75                  80

Gly Pro Thr Ile Gln Ala Glu Val Tyr Asp Thr Val Val Ile Thr Leu
            85                  90                  95

Lys Asn Met Ala Ser His Pro Val Ser Leu His Ala Val Gly Val Ser
        100                 105                 110

Tyr Trp Lys Ala Ser Glu Gly Ala Glu Tyr Asp Asp Gln Thr Ser Gln
    115                 120                 125

Arg Glu Lys Glu Asp Asp Lys Val Phe Pro Gly Gly Ser His Thr Tyr
130                 135                 140

Val Trp Gln Val Leu Lys Glu Asn Gly Pro Met Ala Ser Asp Pro Leu
145                 150                 155                 160

Cys Leu Thr Tyr Ser Tyr Leu Ser His Val Asp Leu Val Lys Asp Leu
            165                 170                 175

Asn Ser Gly Leu Ile Gly Ala Leu Leu Val Cys Arg Glu Gly Ser Leu
        180                 185                 190

Ala Lys Glu Lys Thr Gln Thr Leu His Lys Phe Ile Leu Leu Phe Ala
    195                 200                 205

Val Phe Asp Glu Gly Lys Ser Trp His Ser Glu Thr Lys Asn Ser Leu
210                 215                 220

Met Gln Asp Arg Asp Ala Ala Ser Ala Arg Ala Trp Pro Lys Met His
225                 230                 235                 240

Thr Val Asn Gly Tyr Val Asn Arg Ser Leu Pro Gly Leu Ile Gly Cys
            245                 250                 255

His Arg Lys Ser Val Tyr Trp His Val Ile Gly Met Gly Thr Thr Pro
        260                 265                 270

Glu Val His Ser Ile Phe Leu Glu Gly His Thr Phe Leu Val Arg Asn
    275                 280                 285

His Arg Gln Ala Ser Leu Glu Ile Ser Pro Ile Thr Phe Leu Thr Ala
290                 295                 300

Gln Thr Leu Leu Met Asp Leu Gly Gln Phe Leu Leu Phe Cys His Ile
305                 310                 315                 320

Ser Ser His Gln His Asp Gly Met Glu Ala Tyr Val Lys Val Asp Ser
            325                 330                 335

Cys Pro Glu Glu Pro Gln Leu Arg Met Lys Asn Asn Glu Glu Ala Glu
        340                 345                 350

-continued

Asp Tyr Asp Asp Asp Leu Thr Asp Ser Glu Met Asp Val Val Arg Phe
            355                 360                 365

Asp Asp Asp Asn Ser Pro Ser Phe Ile Gln Ile Arg Ser Val Ala Lys
370                 375                 380

Lys His Pro Lys Thr Trp Val His Tyr Ile Ala Ala Glu Glu Glu Asp
385                 390                 395                 400

Trp Asp Tyr Ala Pro Leu Val Leu Ala Pro Asp Asp Arg Ser Tyr Lys
                405                 410                 415

Ser Gln Tyr Leu Asn Asn Gly Pro Gln Arg Ile Gly Arg Lys Tyr Lys
            420                 425                 430

Lys Val Arg Phe Met Ala Tyr Thr Asp Glu Thr Phe Lys Thr Arg Glu
        435                 440                 445

Ala Ile Gln His Glu Ser Gly Ile Leu Gly Pro Leu Leu Tyr Gly Glu
    450                 455                 460

Val Gly Asp Thr Leu Leu Ile Ile Phe Lys Asn Gln Ala Ser Arg Pro
465                 470                 475                 480

Tyr Asn Ile Tyr Pro His Gly Ile Thr Asp Val Arg Pro Leu Tyr Ser
                485                 490                 495

Arg Arg Leu Pro Lys Gly Val Lys His Leu Lys Asp Phe Pro Ile Leu
            500                 505                 510

Pro Gly Glu Ile Phe Lys Tyr Lys Trp Thr Val Thr Val Glu Asp Gly
        515                 520                 525

Pro Thr Lys Ser Asp Pro Arg Cys Leu Thr Arg Tyr Tyr Ser Ser Phe
    530                 535                 540

Val Asn Met Glu Arg Asp Leu Ala Ser Gly Leu Ile Gly Pro Leu Leu
545                 550                 555                 560

Ile Cys Tyr Lys Glu Ser Val Asp Gln Arg Gly Asn Gln Ile Met Ser
                565                 570                 575

Asp Lys Arg Asn Val Ile Leu Phe Ser Val Phe Asp Glu Asn Arg Ser
            580                 585                 590

Trp Tyr Leu Thr Glu Asn Ile Gln Arg Phe Leu Pro Asn Pro Ala Gly
        595                 600                 605

Val Gln Leu Glu Asp Pro Glu Phe Gln Ala Ser Asn Ile Met His Ser
    610                 615                 620

Ile Asn Gly Tyr Val Phe Asp Ser Leu Gln Leu Ser Val Cys Leu His
625                 630                 635                 640

Glu Val Ala Tyr Trp Tyr Ile Leu Ser Ile Gly Ala Gln Thr Asp Phe
                645                 650                 655

Leu Ser Val Phe Phe Ser Gly Tyr Thr Phe Lys His Lys Met Val Tyr
            660                 665                 670

Glu Asp Thr Leu Thr Leu Phe Pro Phe Ser Gly Glu Thr Val Phe Met
        675                 680                 685

Ser Met Glu Asn Pro Gly Leu Trp Ile Leu Gly Cys His Asn Ser Asp
    690                 695                 700

Phe Arg Asn Arg Gly Met Thr Ala Leu Leu Lys Val Ser Ser Cys Asp
705                 710                 715                 720

Lys Asn Thr Gly Asp Tyr Tyr Glu Asp Ser Tyr Glu Asp Ile Ser Ala
                725                 730                 735

Tyr Leu Leu Ser Lys Asn Asn Ala Ile Glu Pro Arg
            740                 745

<210> SEQ ID NO 3
<211> LENGTH: 2145

```
<212> TYPE: DNA
<213> ORGANISM: Homo sapiens
<220> FEATURE:
<221> NAME/KEY: gene
<222> LOCATION: (1)..(2145)

<400> SEQUENCE: 3
gaattcacgt ggcccagccg gccgtctcgg atcggtaccg aaataactcg tactactctt      60
cagtcagatc aagaggaaat tgactatgat gataccatat cagttgaaat gaagaaggaa     120
gattttgaca tttatgatga ggatgaaaat cagagccccc gcagctttca aaagaaaaca     180
cgacactatt ttattgctgc agtggagagg ctctgggatt atgggatgag tagctcccca     240
catgttctaa gaaacagggc tcagagtggc agtgtccctc agttcaagaa agttgttttc     300
caggaattta ctgatggctc ctttactcag cccttatacc gtggagaact aaatgaacat     360
ttgggactcc tggggccata taagagcaga agttgaag ataatatcat ggtaactttc      420
agaaatcagg cctctcgtcc ctattccttc tattctagcc ttatttctta tgaggaagat     480
cagaggcaag gagcagaacc tagaaaaaac tttgtcaagc ctaatgaaac caaaacttac     540
ttttggaaag tgcaacatca tatggcaccc actaaagatg agtttgactg caaagcctgg     600
gcttatttct ctgatgttga cctggaaaaa gatgtgcact caggcctgat tggacccctt     660
ctggtctgcc acactaacac actgaaccct gctcatggga cacaagtgac agtacaggaa     720
tttgctctgt ttttcaccat ctttgatgag accaaaagct ggtacttcac tgaaaatatg     780
gaaagaaact gcagggctcc ctgcaatatc cagatggaag atcccacttt taagagaat     840 tatcgcttcc atgcaatcaa tggctacata atggatacac tacctggctt agtaatggct     900
caggatcaaa ggattcgatg gtatctgctc agcatgggca gcaatgaaaa catccattct     960
attcatttca gtggacatgt gttcactgta cgaaaaaag aggagtataa aatggcactg    1020
tacaatctct atccaggtgt ttttgagaca gtggaaatgt taccatccaa agctggaatt    1080
tggcgggtgg aatgccttat tggcgagcat ctacatgctg gatgagcac acttttctg    1140 gtgtacagca ataagtgtca gactcccctg gaatggcttc tggacacat tagagatttt    1200 cagattacag cttcaggaca atatggacag tgggcccaa agctggccag acttcattat    1260
tccggatcaa tcaatgcctg gagcaccaag gagccctttt cttggatcaa ggtggatctg    1320
ttggcaccaa tgattattca cggcatcaag acccagggtg cccgtcagaa gttctccagc    1380
ctctacatct ctcagtttat catcatgtat agtcttgatg ggaagaagtg gcagacttat    1440
cgaggaaatt ccactggaac cttaatggtc ttctttggca atgtggattc atctgggata    1500
aaacacaata ttttttaaccc tccaattatt gctcgataca tccgtttgca cccaactcat    1560
tatagcattc gcagcactct tcgcatggag ttgatgggct gtgatttaaa tagttgcagc    1620
atgccattgg gaatggagag taaagcaata tcagatgcac agattactgc ttcatcctac    1680
tttaccaata tgtttgccac ctggtctcct tcaaaagctc gacttcacct ccaagggagg    1740
agtaatgcct ggagacctca ggtgaataat ccaaaagagt ggctgcaagt ggacttccag    1800
aagacaatga agtcacagg agtaactact cagggagtaa aatctctgct taccagcatg    1860
tatgtgaagg agttcctcat ctccagcagt caagatggcc atcagtggac tctctttttt    1920
cagaatggca aagtaaaggt ttttcaggga aatcaagact ccttcacacc tgtggtgaac    1980
tctctagacc caccgttact gactcgctac cttcgaattc accccagag ttgggtgcac    2040 cagattgccc tgaggatgga ggttctgggc tgcgaggcac aggacctcta ctgcggccgc    2100
cagctttcta gaacaaaaac tcatctcaga agaggatctg aatag               2145
```

```
<210> SEQ ID NO 4
<211> LENGTH: 714
<212> TYPE: PRT
<213> ORGANISM: Homo sapiens
<220> FEATURE:
<221> NAME/KEY: PEPTIDE
<222> LOCATION: (1)..(714)

<400> SEQUENCE: 4

Glu Phe Thr Trp Pro Ser Arg Pro Ser Arg Ile Gly Thr Glu Ile Thr
1               5                   10                  15

Arg Thr Thr Leu Gln Ser Asp Gln Glu Ile Asp Tyr Asp Asp Thr
            20                  25                  30

Ile Ser Val Glu Met Lys Lys Glu Asp Phe Asp Ile Tyr Asp Glu Asp
            35                  40                  45

Glu Asn Gln Ser Pro Arg Ser Phe Gln Lys Lys Thr Arg His Tyr Phe
        50                  55                  60

Ile Ala Ala Val Glu Arg Leu Trp Asp Tyr Gly Met Ser Ser Ser Pro
65                  70                  75                  80

His Val Leu Arg Asn Arg Ala Gln Ser Gly Ser Val Pro Gln Phe Lys
                85                  90                  95

Lys Val Val Phe Gln Glu Phe Thr Asp Gly Ser Phe Thr Gln Pro Leu
            100                 105                 110

Tyr Arg Gly Glu Leu Asn Glu His Leu Gly Leu Leu Gly Pro Tyr Ile
            115                 120                 125

Arg Ala Glu Val Glu Asp Asn Ile Met Val Thr Phe Arg Asn Gln Ala
130                 135                 140

Ser Arg Pro Tyr Ser Phe Tyr Ser Ser Leu Ile Ser Tyr Glu Glu Asp
145                 150                 155                 160

Gln Arg Gln Gly Ala Glu Pro Arg Lys Asn Phe Val Lys Pro Asn Glu
                165                 170                 175

Thr Lys Thr Tyr Phe Trp Lys Val Gln His His Met Ala Pro Thr Lys
            180                 185                 190

Asp Glu Phe Asp Cys Lys Ala Trp Ala Tyr Phe Ser Asp Val Asp Leu
            195                 200                 205

Glu Lys Asp Val His Ser Gly Leu Ile Gly Pro Leu Leu Val Cys His
            210                 215                 220

Thr Asn Thr Leu Asn Pro Ala His Gly Arg Gln Val Thr Val Gln Glu
225                 230                 235                 240

Phe Ala Leu Phe Phe Thr Ile Phe Asp Glu Thr Lys Ser Trp Tyr Phe
                245                 250                 255

Thr Glu Asn Met Glu Arg Asn Cys Arg Ala Pro Cys Asn Ile Gln Met
            260                 265                 270

Glu Asp Pro Thr Phe Lys Glu Asn Tyr Arg Phe His Ala Ile Asn Gly
            275                 280                 285

Tyr Ile Met Asp Thr Leu Pro Gly Leu Val Met Ala Gln Asp Gln Arg
290                 295                 300

Ile Arg Trp Tyr Leu Leu Ser Met Gly Ser Asn Glu Asn Ile His Ser
305                 310                 315                 320

Ile His Phe Ser Gly His Val Phe Thr Val Arg Lys Lys Glu Glu Tyr
                325                 330                 335

Lys Met Ala Leu Tyr Asn Leu Tyr Pro Gly Val Phe Glu Thr Val Glu
            340                 345                 350

Met Leu Pro Ser Lys Ala Gly Ile Trp Arg Val Glu Cys Leu Ile Gly
```

```
                    355                 360                 365
Glu His Leu His Ala Gly Met Ser Thr Leu Phe Leu Val Tyr Ser Asn
                370                 375                 380

Lys Cys Gln Thr Pro Leu Gly Met Ala Ser Gly His Ile Arg Asp Phe
385                 390                 395                 400

Gln Ile Thr Ala Ser Gly Gln Tyr Gly Gln Trp Ala Pro Lys Leu Ala
                405                 410                 415

Arg Leu His Tyr Ser Gly Ser Ile Asn Ala Trp Ser Thr Lys Glu Pro
                420                 425                 430

Phe Ser Trp Ile Lys Val Asp Leu Leu Ala Pro Met Ile Ile His Gly
                435                 440                 445

Ile Lys Thr Gln Gly Ala Arg Gln Lys Phe Ser Ser Leu Tyr Ile Ser
                450                 455                 460

Gln Phe Ile Ile Met Tyr Ser Leu Asp Gly Lys Lys Trp Gln Thr Tyr
465                 470                 475                 480

Arg Gly Asn Ser Thr Gly Thr Leu Met Val Phe Phe Gly Asn Val Asp
                485                 490                 495

Ser Ser Gly Ile Lys His Asn Ile Phe Asn Pro Pro Ile Ile Ala Arg
                500                 505                 510

Tyr Ile Arg Leu His Pro Thr His Tyr Ser Ile Arg Ser Thr Leu Arg
                515                 520                 525

Met Glu Leu Met Gly Cys Asp Leu Asn Ser Cys Ser Met Pro Leu Gly
                530                 535                 540

Met Glu Ser Lys Ala Ile Ser Asp Ala Gln Ile Thr Ala Ser Ser Tyr
545                 550                 555                 560

Phe Thr Asn Met Phe Ala Thr Trp Ser Pro Ser Lys Ala Arg Leu His
                565                 570                 575

Leu Gln Gly Arg Ser Asn Ala Trp Arg Pro Gln Val Asn Asn Pro Lys
                580                 585                 590

Glu Trp Leu Gln Val Asp Phe Gln Lys Thr Met Lys Val Thr Gly Val
                595                 600                 605

Thr Thr Gln Gly Val Lys Ser Leu Leu Thr Ser Met Tyr Val Lys Glu
                610                 615                 620

Phe Leu Ile Ser Ser Ser Gln Asp Gly His Gln Trp Thr Leu Phe Phe
625                 630                 635                 640

Gln Asn Gly Lys Val Lys Val Phe Gln Gly Asn Gln Asp Ser Phe Thr
                645                 650                 655

Pro Val Val Asn Ser Leu Asp Pro Pro Leu Leu Thr Arg Tyr Leu Arg
                660                 665                 670

Ile His Pro Gln Ser Trp Val His Gln Ile Ala Leu Arg Met Glu Val
                675                 680                 685

Leu Gly Cys Glu Ala Gln Asp Leu Tyr Cys Gly Arg Gln Leu Ser Arg
                690                 695                 700

Thr Lys Thr His Leu Arg Arg Gly Ser Glu
705                 710

<210> SEQ ID NO 5
<211> LENGTH: 31
<212> TYPE: DNA
<213> ORGANISM: Homo Sapiens
<220> FEATURE:
<221> NAME/KEY: prim_transcript
<222> LOCATION: (1)..(31)

<400> SEQUENCE: 5
```

```
gtggcccagc cggccagcca ccagaagata c                                 31

<210> SEQ ID NO 6
<211> LENGTH: 26
<212> TYPE: DNA
<213> ORGANISM: Homo Sapiens
<220> FEATURE:
<221> NAME/KEY: prim_transcript
<222> LOCATION: (1)..(26)

<400> SEQUENCE: 6
aatgcggccg ctcatcttgg ttcaat                                       26

<210> SEQ ID NO 7
<211> LENGTH: 30
<212> TYPE: DNA
<213> ORGANISM: Homo Sapiens
<220> FEATURE:
<221> NAME/KEY: prim_transcript
<222> LOCATION: (1)..(30)

<400> SEQUENCE: 7
aaggtaccga ataactcgt actactcttc                                    30

<210> SEQ ID NO 8
<211> LENGTH: 27
<212> TYPE: DNA
<213> ORGANISM: Homo Sapiens
<220> FEATURE:
<221> NAME/KEY: prim_transcript
<222> LOCATION: (1)..(27)

<400> SEQUENCE: 8
aagcggccgc agtagaggtc ctgtgcc                                      27
```